US012533490B2

(12) United States Patent
Vilkomerson

(10) Patent No.: US 12,533,490 B2
(45) Date of Patent: Jan. 27, 2026

(54) CATHETER PLATFORM FOR THERAPY AND MEASUREMENT

(71) Applicant: DVX LLC, Princeton, NJ (US)

(72) Inventor: David Vilkomerson, Princeton, NJ (US)

(73) Assignee: DVX LLC, Princeton, NJ (US)

( * ) Notice: Subject to any disclaimer, the term of this patent is extended or adjusted under 35 U.S.C. 154(b) by 0 days.

(21) Appl. No.: 18/780,184

(22) Filed: Jul. 22, 2024

(65) Prior Publication Data

US 2025/0041565 A1 Feb. 6, 2025

Related U.S. Application Data

(60) Provisional application No. 63/629,951, filed on Jul. 31, 2023.

(51) Int. Cl.

*A61M 25/01* (2006.01)
*A61M 25/04* (2006.01)
*A61M 25/00* (2006.01)

(52) U.S. Cl.

CPC ........ *A61M 25/0122* (2013.01); *A61M 25/04* (2013.01); *A61M 2025/006* (2013.01); *A61M 25/01* (2013.01)

(58) Field of Classification Search

CPC .............. A61M 25/0122; A61M 25/04; A61M 2025/006; A61M 25/1002; A61M 25/1011; A61M 2025/1015; A61M 2025/1047; A61M 25/0133; A61M 25/0155; A61M 2025/1084

See application file for complete search history.

(56) References Cited

U.S. PATENT DOCUMENTS 4,983,165 A * 1/1991 Loiterman ......... A61M 25/1011 604/95.03
6,162,171 A * 12/2000 Ng ....................... A61B 1/0055 600/101
7,963,911 B2 * 6/2011 Turliuc .................. A61B 1/041 600/114
2009/0030510 A1 * 1/2009 Ho ................... A61B 17/12136 623/2.11

(Continued)

FOREIGN PATENT DOCUMENTS

JP 2014061163 A * 4/2014

*Primary Examiner* — Bhisma Mehta
*Assistant Examiner* — Anna E Goldberg-Richmeier
(74) *Attorney, Agent, or Firm* — Princeton IP Law LLC

(57) ABSTRACT

Techniques described herein relate to a catheter platform for carrying a medical device into inside a body. The catheter platform may include a catheter, which during use, is inserted into a body lumen. The catheter platform may include at least two extensile protrusions extending from opposite walls of the catheter and configured to expand outwardly in opposite directions to be in touch with the walls of the body lumen to aim the medical device and provide stability of the catheter. In an embodiment in which the body lumen is blood vessel, the catheter platform is configured to preserve the cross-section of the lumen such that the effect on the blood flow is minimized. A variety of applications may be enabled by the catheter platform, including therapy, measurement, or other procedures that may require the medical device to be left inside the body for an extended time period.

18 Claims, 3 Drawing Sheets

(56) References Cited

U.S. PATENT DOCUMENTS

| | | | | |
|---|---|---|---|---|
| 2015/0081006 | A1* | 3/2015 | Chuter | B32B 27/12 623/1.11 |
| 2021/0308431 | A1* | 10/2021 | Jalgaonkar | A61M 25/1002 |
| 2022/0313947 | A1* | 10/2022 | Petros | A61B 5/6885 |

* cited by examiner

CATHETER PLATFORM FOR THERAPY AND MEASUREMENT

RELATED APPLICATIONS

This application claims the benefit under 35 U.S.C. § 119(e) of U.S. Provisional Application No. 63/629,951, filed Jul. 31, 2023, the entire contents of which are incorporated herein by reference.

FIELD

This technology relates to catheter platforms, and more particularly to catheter platforms for therapy and measurement.

BACKGROUND

Catheters are tubes placed into the body. As all living tissue requires blood, the circulatory system reaches all parts of the body and thus a catheter placed in it can be guided to come close to any target tissue. For example, catheters are used to infuse drugs and nutrients, to extract and infuse blood, to measure blood pressure and gases, and to carry devices, stents or balloons or extractors, to correct circulatory problems, e.g. to open or expand stenotic regions of the coronary arteries, close arteriovenous malformations, extract clots following strokes. Catheters can also be placed in other lumens, for example in the ureters and urethras in the genitourinary system, in the esophagus and colon in the digestive system, passages of the sinus, etc. Other uses of catheters include catheter-based ultrasound or optical measurement from within the lumens of the body.

SUMMARY

The present disclosure relates to techniques for catheter platforms for therapy and measurement. In an embodiment, the techniques provide an apparatus for carrying a medical device into inside a body. The apparatus comprises: a catheter, which during use, is inserted into the body through a body lumen; and at least two extensile protrusions extending from walls of the catheter and configured to expand outwardly in opposite directions to be in touch with walls of the body lumen to provide stability of the catheter while inside the body.

In an embodiment, the techniques provide a method for performing a medical procedure within a body, the method comprising: inserting a catheter into a lumen in the body, wherein the catheter comprises at least two extensile protrusions extending from walls of the catheter, the at least two extensile protrusions being at a deflated state when inserted; inflating the at least two extensile protrusions outwardly in opposite directions to be in touch with walls of the body lumen to aim a medical device disposed on the catheter at a desired angle; and operating the medical device to perform the medical procedure within the body.

BRIEF DESCRIPTION OF DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

DETAILED DESCRIPTION

Figure 1:
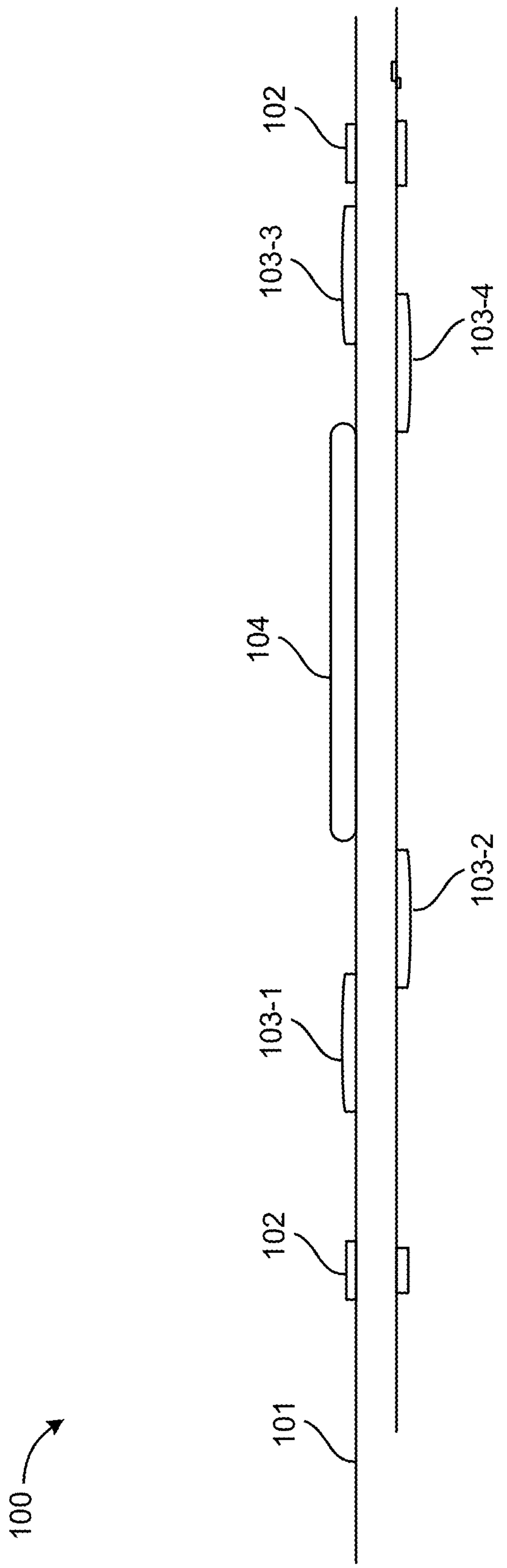
FIG. 1 illustrates a schematic diagram of an example catheter platform on which the extensile protrusions are in a deflated state, according to some embodiments.

Existing catheter-based systems for therapy or measurement typically use a catheter system to carry a medical device into a target area in the body to perform a medical procedure, such as directing energy to the body tissue for therapy or taking measurement. These uses often require constant skilled imaging to ensure proper placement and aiming of the medical device. For example, as patients may move and the medical device inside a blood vessel may have moved, the position or angle of the medical device may need to be adjusted once inside the body. Further, because of the movement introduced by the patients or the movement of the medical device inside the blood vessel, the medical procedure (e.g., therapy or measurement) are episodic and cannot last an extended period of time.

The existing systems attempt to stabilize the catheter inside the body by using balloons. In these systems, balloons are configured as collars around the catheter. Balloons are inflated via fluid conducted by lumens in the catheter, and expand in multiple directions along the surface of the balloons to be in touch with the vessel walls to stabilize the catheter and the medical device thereon. These balloon-based systems have some drawbacks. For example, a collar-shaped balloon inflates uniformly in multiple directions around the surface of the balloon thus the catheter can only be centered along the axis of the lumen, making the catheter inflexible in its position or aiming angle. Further, because the collar-shaped balloons wrap around the catheter, the balloons may be specially designed such that, when inflated, the balloons will not block the blood flow in the vessel.

Accordingly, the inventor has developed technologies that include a unique catheter platform that can be stably positioned and aimed from within blood vessels or other body lumens. Body lumen may include blood vessel in circulatory system, or other body lumens, such as the ureters and urethras in the genitourinary system, the esophagus and colon in the digestive system, passages of the sinus, etc. or other body lumens. Body lumen may include naturally occurring body lumens or artificial body lumens, such as lumen inside a coronary stent. The catheter platform makes possible catheter-mounted therapeutic ultrasound transducers (and other energy sources) to treat tissues from nearby blood vessels, eliminating the distortion and attenuation to the beams caused by having to go through the body. Once aimed and stabilized, the catheter platform can be left in place to provide continuous therapy and or measurement.

The catheter platform has a catheter provided with at least two extensile protrusions. Examples of a catheter may include a tube which can be inserted into a body with or without incision. For example, in convention methods, a catheter can be inserted into blood vessel via a small incision in the skin followed by a needle into the blood vessel through which a "guide wire" is placed and then a "dilator" is threaded over the wire into the vessel to expand the vessel opening and then the catheter is introduced into the vessel. For other body lumens, a catheter may be introduced without needing incision.

The two extensile protrusions may extend from the catheter and are configured to, when inflated, expand outwardly in opposite directions. For example, the catheter can be stably positioned and oriented by selectively lengthening and shortening each individual extensile protrusion mounted on the catheter exterior to be in touch with the vessel wall. This allows stable positioning and orientation without significantly affecting blood flow. The extensile protrusion may be made of a balloon in some examples. The extensile protrusion may be made of mechanical "fingers" made of nitinol elements or other suitable materials, in some examples.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended. It should be further appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates a schematic diagram (shown in longitudinal cross-section) of an example catheter platform 100 on which the extensile protrusions, e.g., balloons 103 are in a deflated state, according to some embodiments. The catheter platform 100 includes a catheter 101 (e.g., a tube) having multiple openings (in its walls) from which respective balloons 103 extend. As shown, extensile protrusions, e.g., balloons 103 are in their deflated state, so that they are furled flat against the exterior walls of the catheter. This allows the catheter to be inserted into or removed from the body (e.g., through the body lumen).

In FIG. 1, the catheter platform 100 may also include a medical device 104 for performing a medical procedure once the medical device 104 has reached a target area in the body. As shown, the medical device 104 is disposed on the catheter between a first pair of balloons (103-1, 103-2) and a second pair of balloons (103-3, 103-4). Each pair of balloons may have an opposite orientation, e.g. upper balloon and a lower balloon. For example, the first pair has an upper balloon 103-1 and lower balloon 103-2; the second pair has an upper balloon 103-3 and a lower balloon 103-4. It is appreciated that the balloons may have various positions and arrangement as will be further described.

The catheter system 100 may further include one or more markers 102, which can be used in guiding the catheter through the body under imaging guidance (e.g., using an X-ray). As shown, the one or more markers 102 may be disposed on each side of the balloon pairs (e.g., to the left of the 103-1, 103-2 balloon pair, and to the right of the 102-3, 103-4 balloon pair). In some embodiments, the markers 102 may be metal rings or have other suitable configurations.

Figure 2:
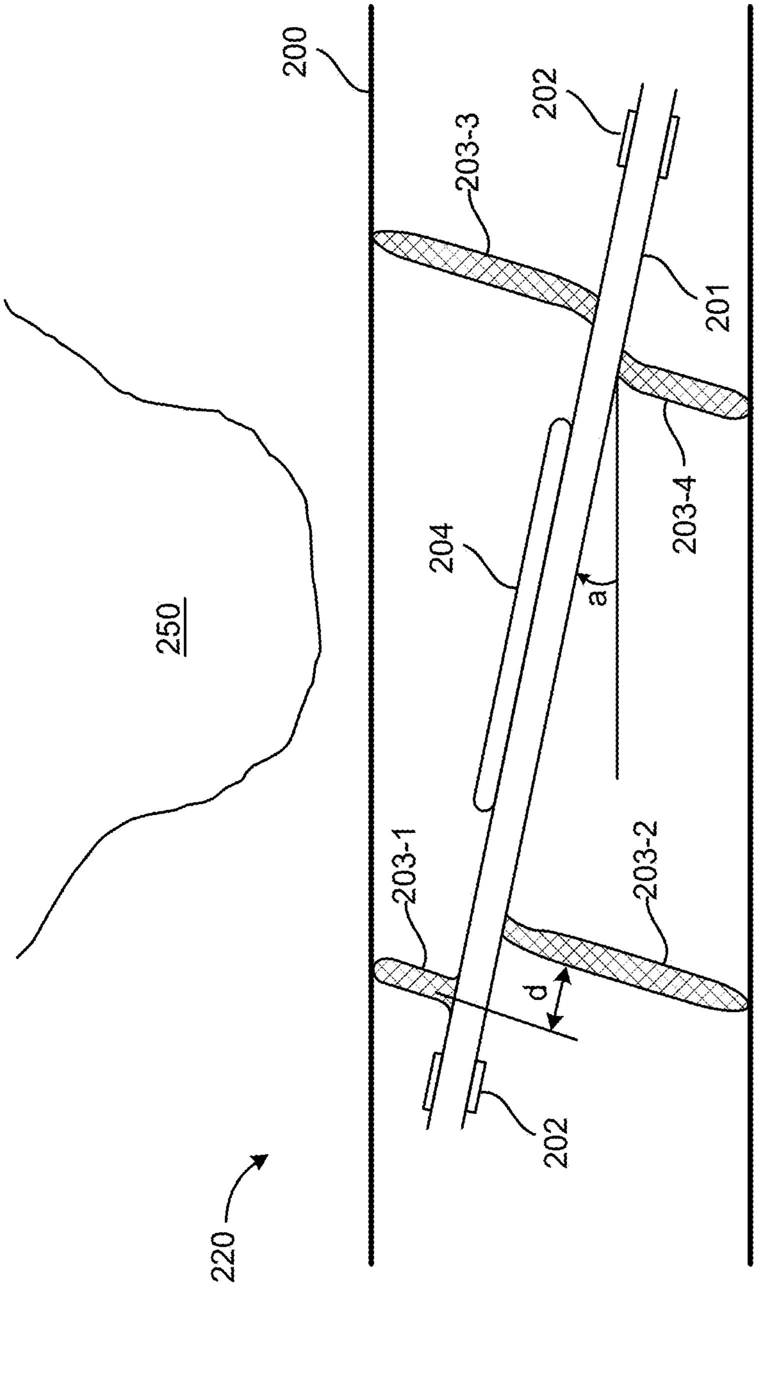
FIG. 2 illustrates a schematic diagram of an example catheter platform on which the extensile protrusions are in an inflated state, according to some embodiments.

FIG. 2 illustrates a schematic diagram of an example catheter platform 220 on which the extensile protrusions are in an inflated state, according to some embodiments. The catheter platform 200 may be catheter platform 100 with the balloons being inflated. During use, the catheter system 220 is inserted into a body lumen. The extensile protrusions, e.g., balloons 203, have at least two extensile protrusions (a pair), e.g., balloons 203-1, 203-2, that when inflated, expand outwardly in opposite directions to be in touch with opposite walls of the vessel 200 to provide stability of the catheter while inside the body.

In some embodiments, the two balloons in a pair of ballons may be inflated at different lengths. As shown in FIG. 2, when inflated, balloon 203-1 is shorter than balloon 203-2. This may be controlled by providing different pressures onto the balloons. Existing technologies on pressurizing balloons may be used and adapted such that different control systems are applied to different balloons to provide different pressures, causing the balloons to expand at different lengths. An example of balloon pressuring systems may include the Boston Scientific Encore 26, which is a typical (calibrated) inflator device used with balloon-catheters. The pressuring system may include a gauge by which the pressure in the catheter-balloon is determined, and a luer lock tube connection, in some examples.

As shown in FIG. 2, inflating the balloons to different lengths may allow aiming and stabilizing the catheter (or the medical device thereon). For example, the catheter may be aimed at a desired angle relative to the vessel 200. As shown, the catheter is aimed at an angle a with respect to the axis of the vessel. Once the catheter is properly aimed, the catheter can also be stabilized via the balloons, such as balloons 203. For example, the two pairs of balloons (203-1/203-2; 203-3/203-4) are inflated to expand outwardly to be in touch with the walls of the vessel, to restrict the catheter (and medical device thereon) from movement.

In some embodiments, the aiming of the catheter can be monitored or guided by using contrast agent (as highlighted in grayscale) inside the ballons. This enables an operator to see the balloon's inflation via imaging techniques (e.g., X-ray or ultrasound) and properly place and aim medical device 204.

The configurations of the catheter platform in FIGS. 1-2 are further explained. The balloons 103, 203 may be positioned in various configurations, and the medical device 104, 204 may be placed at various positions along the catheter calls. For example, the two balloons 203-1 and 203-2 in the pair may be staggered in position along the length of the catheter. As shown, balloons are positioned staggered by a distance d. Staggered balloons may be advantageous in minimally affecting the blood flow in some applications by minimizing the cross-section of the catheter platform at any point along the vessel. In other variations, the two balloons in a pair may be positioned at the same location (not staggered) along the catheter, where the openings for the two balloons are on opposite walls of the catheter.

Figure 4:
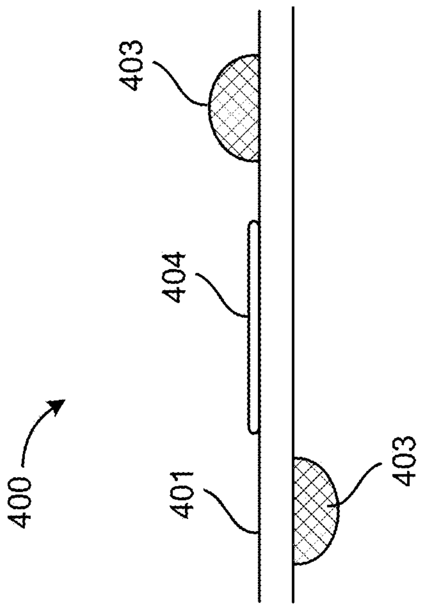
FIG. 4 illustrates a partial view of a variation of an example catheter, according to some embodiments.

In some embodiments, the medical device is disposed between two pairs of balloons. For example, medical device 204 (FIG. 2) is disposed between the balloon pair (203-1, 203-2) and balloon pair (203-3, 203-4) such that the two pairs of balloons are on opposite sides of the medical device. In some variations, the medical device may be placed proximate to the pair of balloons (e.g., on either side of the balloons). In other variations, the two balloons in the pair of balloons may be positioned apart from each other on opposite sides of the medical device. For example, FIG. 4 shows a configuration in which two extensile protrusions, e.g., balloons 403, are placed on opposite walls of the catheter 401 and on opposite sides of the medical device 404.

The various positions and/or arrangement of the balloons and the medical device as may be configured in catheter platforms 100 (FIG. 1) and 220 (FIG. 2) allow various medical procedures to be performed. For example, in FIG. 2, medical device 204 is placed proximate to a target tissue

250 such that a medical procedure can be performed. The target tissue may be outside the lumen as ultrasound and other forms of energy can propagate through the lumen wall. In non-limiting examples, a medical device may be an energy directing device, e.g., a transducer such as a laser that transduces electrical signals into light and affects the tissue for therapeutic treatment. In other examples, medical device 204 may be an ultrasonic transducer array that uses ultrasound waves to treat certain conditions in the tissue or other anatomical part of a body.

With improved aiming (orientation) and stability, the catheter platform can be used in other therapeutic and measurement applications, such as ablation and histotripsy using high-intensity focused ultrasound, or, by utilizing fiber optics in the catheter photodynamic therapy, photoacoustic imaging, and optical measurements.

In some non-limiting examples, medical device 104, 204 may each be a transducer that can be used to take measurement related to an anatomical part of a body. For example, a diffraction-grating transducer ("DGT") disclosed in "A Flexible Implantable Sensor for Postoperative Monitoring of Blood Flow," Journal of Ultrasound in Medicined 289:S60, can be wrapped around the catheter and used to measure the blood flow by emitting ultrasound beams and receiving signals reflected by scatters in the blood flow.

In some non-limiting examples, the angle of transmitted ultrasound beam may be affected by the angle of the transducer (see U.S. Pat. Nos. 5,488,953 and 5,540,230 to Vilkomerson). The angle of the transducer, which is disposed on the catheter, may be facilitated by the lengths (or different lengths) of the balloons, when inflated, as described above and further herein. In other non-limiting examples, medical device 104, 204 may include a transducer array of a double-beam DGT on a central line placed in the superior vena cava to measure blood flow in the nearby ascending aorta, providing an important measure, cardiac output. This procedure is described in U.S. Published Patent Application No. 20160000403 to Vilkomerson, which is incorporated herein by reference.

In other variations, medical device 104, 204 may be non-energy directing device. For example, the medical device may withdraw materials from tissue (e.g., withdrawing cancer cells or materials from a cyst) to determine conditions of the tissue or determine treatment based on the cells or materials in the tissue.

In some embodiments, the catheter system as disclosed in FIGS. 1-2 may be of conventional construction, e.g. of Pebax or Nylon, etc., with a large central lumen for a guide wire and multiple openings in the catheter wall from which the balloons extend. The balloons, 103 and 203, can be made by any suitable conventional methods, such as dipping. In some examples, balloons may be made of latex material, allowing elongation (e.g., expanding radially with respect to the catheter, as shown in FIG. 2) without bursting, to multiple times of its original length (e.g., 7 times or higher). This enables the catheter to be at a high angle with respect to the vessel axis. For example, as shown in FIG. 2, the ratio in length of the longest to the shortest balloon (when inflated) may be three to one, resulting in a high a value.

Figure 3:
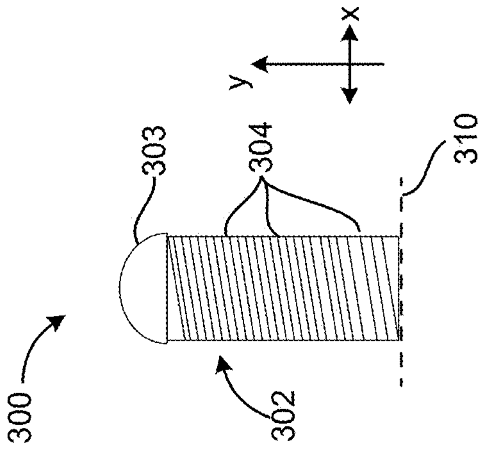
FIG. 3 illustrates an example configuration of a balloon that may be used as an extensile element in the catheter platforms in FIGS. 1-2, according to some embodiments.

The inventor has recognized and appreciated that it may be critical that the balloons not restrict the blood flow in the blood vessel. In such case, it may be desirable to have the extensile protrusion expanding only in the lengthwise (axial) direction while restricting expansion in the radial direction. FIG. 3 illustrates an example configuration of a balloon that may be used in the catheter platforms in FIGS. 1-2, according to some embodiments. In FIG. 3, a balloon 300 may have a cylindrical body 302, which can expand only in the length/axial direction (shown in y) and not in the radial direction (shown in x), where the x direction is substantially in parallel to the axis of the catheter 310.

These characteristics may be achieved by using materials that may expand in one direction only and yet allows the balloon to be deflated such that it can be furled flat, allowing the catheter to be inserted into the lumen. Some example configurations have these characteristics will be further described.

As shown in FIG. 3, the cylindrical body 302 may comprise of thin wires 304 that are spirally wound around the balloon body such that inflation pressure lengthens the cylinder (in its axial direction, e.g., y direction) rather than expanding in diameter (in x direction). This preserves the cross-sectional lumen of the vessel so as to prevent the balloons from blocking the lumen or significantly affecting the blood flow in the vessel. Other variations of the balloon construction may be possible. For example, a mesh wire or lattice of suitable materials, whether conductive or non-conductive, may be used to construct the wall of the balloon.

With further reference to FIG. 3, balloon 300 may have a top 303. In some embodiments, the top of the balloon may be made conductive, for example, by plating on it a thin metallic layer. The spiral wire 304 of a balloon can be conductive and connected to conductors in the wall of the catheter 310 so that the top and the cylindrical body of the balloon can act as an electrode to form an electrical path, where a return path is formed through the body (e.g., body tissue). In other configurations in which non-conductive materials are used for cylindrical body of the balloon, conductive coating may be applied to the balloon body so that the balloon remains flexible and can be deflated or inflated.

Balloon electrodes may enable various applications. For example, in a given medical procedure, the catheter platform as described herein may have the balloons inflated to be in touch with a brain region, where the conductive balloons make a conductive path into the brain. This conductive path allows electrical current to be introduced into the brain (e.g., to stimulate the brain for therapeutic effects or other treatment). The conductive path may also allow measurement of electrical current in the brain.

Other uses of balloon electrodes include using the electrodes to detect neural signals, which is disclosed in Mitchell et al, Assessment of Safety of a Fully Implanted Endovascular Brain-computer Interface for Severe Paralysis in 4 Patients, JAMA Neurology 2023, 80(3) 278, and is incorporated herein by reference. Other uses of the balloon electrodes may also include injecting signals for neuromodulation, which is disclosed in Schiff N D, et al., Behavioral improvements with thalamic stimulation after severe traumatic brain injury, Nature 2007PMID 17671503, which is incorporated herein by reference.

In comparing to existing techniques in using electrodes inside the body, the catheter platform as disclosed herein has advantages in mobility and versatile uses. For example, the electrodes (e.g., balloon electrodes) can be freely moved into or out of the body, e.g., by inserting the catheter into the body or removing it from the body, in the manners as described in the present disclosure. The balloon electrodes can be connected or disconnected (by inflating or deflating) at any time.

It is appreciated that variations of the catheter platforms as described in embodiments in FIGS. 1-2 may be possible. For example, the diameter and length of the catheter platform, and the size of the balloons may be determined by the target vessel anatomy. FIG. 4 illustrates a partial view of a variation of a catheter platform 400, according to some embodiments. Catheter platform 400 is similar to catheter platform 100 (FIG. 1) and 200 (FIG. 2), with the difference being that it is a simplified configuration that is easier to fabricate. As shown in FIG. 4, catheter platform 400 has a catheter 401 and staggered half balloons 403 sandwiching the medical device 404 (e.g., transducer array) to hold the medical device stable. Despite the lack of aiming feature (e.g., forming an angle as described in embodiments in FIG. 2), catheter platform 400 can provide stability for the transducer array.

In the configuration in FIG. 4, the balloons 403 may each have a shape of a dome. When inflated, the balloons may expand in multiple directions around the surface of the dome. Although the balloons may occlude more of the vessel lumen, for some blood vessels (e.g., with larger diameters), this configuration may still have minimal effect on the blood flow.

The catheter platform as described in various embodiments in FIGS. 1-4 may be used to perform a medical procedure in an anatomical part of a body by performing one or more steps. For example, the steps may include inserting a catheter through a naturally occurring body lumen (e.g., blood vessel). The catheter may be configured in a similar manner as described in embodiments in FIGS. 1-4. For example, the catheter may include at least two balloons extending from the walls of the catheter (e.g., ballons 103-1, 103-2 in FIG. 1; balloons 203-1, 203-2 in FIG. 2, balloons 403 in FIG. 4), the at least two balloons being at a deflated state. Further, the at least two balloons may be inflated outwardly in opposite directions in a similar manner as described in embodiments in FIGS. 1-4. When inflated, the balloons may expand in different lengths to aim a medical device (e.g., 104 in FIG. 1; 204 in FIG. 2; 404 in FIG. 4) disposed on the catheter at a desired angle (e.g., angle a shown in FIG. 2). Once the medical device is aimed properly, the medical device may be operated to perform a medical procedure over the anatomical part of the body. Additionally, the medical device may also be stabilized by the at least two balloons, and/or additional balloons as described in embodiments in FIGS. 1-4.

In some brain applications that may utilize the catheter platform as described in the present disclosure, the medical device disposed on the catheter may include piezoelectric curved or cylindrical piezoelectric transducers to insonate, for example, an area along a vessel wall next to a brain tumor. When the catheter platform is aimed and stabilized, ultrasound in conjunction with microbubbles may be generated to allow the passage of a therapeutic agent through the blood-brain barrier. Such therapy is disclosed in Qui, W, Ultrasound for the Brain: A Review of Physical and Engineering Principles, and Clinical Applications, IEEE T-UFFR 68 (6) 2021, which is incorporated herein by reference.

In some applications that may use the catheter platform as described in the present disclosure, the catheter platform (e.g., 100 in FIG. 1, 200 in FIG. 2) is inserted into the circulatory system with all the balloons being in a deflated state (such as shown in FIG. 1). This allows the catheter to fit through an introducing sheath (introducer) usually used for introducing conventional catheters into the vessels of the body. The marker bands, 202 (FIG. 2) are visible in the imaging system in use to “mark” the location of the catheter. Because the distance from the markers to the medical device is known, the location of the medical device (e.g., 204 in FIG. 2) can be determined based on the location of the marker. These markers are used to advance the catheter under imaging guidance (e.g., X-ray, MRI, ultrasound) to the treatment location.

The positioning balloons (e.g., 203 in FIG. 2) are then individually filled via openings in the catheter respectively for the balloons. The medium used for filling the balloons may be a “contrast agent” appropriate for the particular kind of image guidance, e.g. x-ray contrast medium for X-ray guidance, ultrasound contrast medium for ultrasound guidance. As shown in FIG. 2, the four balloons 203 can be individually inflated to expand in different lengths (or same length) to aim and/or position the medical device 204 to the area under treatment or measurement. The catheter position and angle, using the balloon structure of FIG. 3, is monitored via the imaging guidance, and controlled by the calibrated pressure inflator, which is commercially available. When the catheter is to be located at another position, needs to be withdrawn, the balloons (e.g., 203 in FIG. 2) are deflated allowing the catheter platform to be repositioned or withdrawn from the circulatory system via the introducer.

The catheter platform as described in the present disclosure can further be used for a variety of applications. For example, if there is a small tumor that has been found by imaging on the inside of a lumen, the catheter carrying an ultrasound transducer capable of ablating the tumor can be introduced into the lumen near the tumor, in a similar manner as described above. For example, balloons (e.g., 103 in FIG. 1) are deflated to allow the catheter to be inserted into the lumen. The catheter is introduced into the lumen near the tumor and is advanced toward the tumor by image-guidance observing the position of the markers (e.g., marker bands 202 in FIG. 2).

In some embodiments, two marker bands (e.g., 202 in FIG. 2) may be positioned on opposite sides of a transducer at the same distance from the respective opposite side. In other words, the mid-point of the two marker bands may correspond with the center of the transducer. When the marker bands are visible on either side of the targeted tumor, the catheter is adjusted, under imaging guidance, so that the distance from each marker band to the nearest edge of the tumor is the same. This ensures that the ablating ultrasound transducer (e.g., 204 in FIG. 2) is exactly opposite and centered on the tumor. The special extensile balloons (e.g., 203 in FIG. 2) are pressurized via inflation of their individual lumens by pumping contrast material into them. The position and angle of the medical device (e.g., 204 in FIG. 2) can be adjusted in a similar manner as described in FIG. 2 (e.g., by inflating different balloons 203 to different lengths) so that the catheter is level and at the optimal distance (focus) to ablate the tumor. After ablation (or other procedures using the medical device, e.g., 204 in FIG. 2), the balloons (e.g., 203 in FIG. 2) are evacuated (deflated) for the catheter to be moved to the next target or withdrawn from the vessel.

In the above application, alternatively, the extensile protrusions (e.g., balloons 203) may be left inside the vessel inflated. As described in various embodiments above, the balloons are shaped and configured to minimize affecting the blood flow in the vessel if part of the circulatory system. With the catheter left in place, this allows monitoring or repeating the procedure if needed in the days following, without the need for additional imaging for positioning.

In some variations, rather than using an ablating ultrasound transducer, some other energy transmitting devices, such as a laser, RF transmitter, radioactive pellet, etc., would similarly be positional using the catheter platform described in the present disclosure to eliminate the tumor. In other variations, device 204 may include an observational element, or a sampling mechanism as all such devices would be useful with the catheter platform.

In some applications, tissues or other vessels not immediately adjacent to the catheter's blood vessel can also be treated or measured by adding a variable-focus ultrasound lens to the catheter's ultrasound transducer. The lens may include a lens-shaped balloon that changes its curvature by its degree of inflation and changes its refractive index by using inflating fluids of differing acoustic velocity. Thus the focal length of the lens can be varied to reach tissues at different distances from the catheter platform.

The various embodiments of catheter platforms described in the present disclosure provide advantages over existing catheter-based systems in that the catheter (and the medical device disposed thereon) may be aimed at a desirable angle with respect to the axis of the lumen. Further, the balloons provided on the catheter may provide stability for the medical device to allow a variety medical procedures to be performed. Further, the structure and positional arrangement of balloons minimize the effect on the blood flow in the vessel. This advantage, along with the positional stability of the catheter platform, allows extended treatments and measurements while leaving the catheter platform inside the body for a long time period. Veins have been shown to tolerate long-term catheter use such as for dialysis catheters and pacemaker leads.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

The invention claimed is:

1. An apparatus for carrying a medical device into inside a body, the apparatus comprising:

a catheter, which is configured to be inserted into the body through a body lumen; and at least two extensile protrusions disposed directly on opposite walls of a shaft of the catheter and extending therefrom and further configured to expand outwardly perpendicularly to the shaft of the catheter in opposite directions to be in touch with walls of the body lumen to provide stability of the catheter while inside the body;

wherein the at least two extensile protrusions are each structured to include an extensile cylindrical body and configured to expand in an axial direction of the cylindrical body, the cylindrical body comprising materials such that, when pressurized, the cylindrical body expands in a perpendicular direction with respect to an axis of the catheter and resists expansion in a parallel direction with respect to the axis of the catheter.

2. The apparatus of claim 1, wherein the at least two extensile protrusions are staggered in position along a length of the catheter.

3. The apparatus of claim 2, wherein the catheter is provided with a medical device disposed between the at least two extensile protrusions.

4. The apparatus of claim 1, wherein the catheter is provided with a medical device disposed proximate to the at least two extensile protrusions.

5. The apparatus of claim 1, wherein the at least two extensile protrusions are positioned proximate to each other to form a first pair of extensile protrusions and extend respectively from opposite walls of the catheter.

6. The apparatus of claim 5, further includes a second pair of extensile protrusions having two extensile protrusions extending respectively from opposite walls of the catheter, the first pair of extensile protrusions and the second pair of extensile protrusions being on opposite sides of a medical device disposed on the catheter along a length of the catheter.

7. The apparatus of claim 1, wherein, when pressurized, the cylindrical body of each of the at least two extensile protrusions is configured to expand in the axial direction and resist expansion in a radial direction of the cylindrical body.

8. The apparatus of claim 7, wherein at least one of the at least two extensile protrusions comprises a conductive top configured to form an electrode.

9. The apparatus of claim 1, wherein a first extensile protrusion of the at least two extensile protrusions is configured to expand at a first length and a second extensile protrusion of the at least two extensile protrusions is configured to expand at a second length different from the first length.

10. The apparatus of claim 9, wherein each of the first and second extensile protrusions of the at least two extensile protrusions is configured to be individually controlled by a respective pressure device applying different pressures to the extensile protrusion.

11. A method for performing a medical procedure within a body, the method comprising:

inserting a catheter into a body lumen, wherein the catheter comprises at least two extensile protrusions disposed directly on and extending from opposite walls of a shaft of the catheter and further configured to expand outwardly perpendicularly to the shaft of the catheter in opposite directions to be in touch with walls of the body lumen to provide stability to the catheter while inside the body, wherein the at least two extensile protrusions are each structured to include an extensile cylindrical body and configured to expand in an axial direction of the cylindrical body, the cylindrical body comprising materials such that, when pressurized, the cylindrical body expands in a perpendicular direction with respect to an axis of the catheter and resists expansion in a parallel direction with respect to the axis of the catheter, the at least two extensile protrusions being at a deflated state;

inflating the at least two extensile protrusions outwardly in opposite directions to be in touch with the walls of the body lumen to aim a medical device disposed on the catheter at a desired angle; and operating the medical device to perform the medical procedure within the body.

12. The method of claim 11, wherein the at least two extensile protrusions are staggered in position along a length of the catheter.

13. The method of claim 12, wherein the medical device is disposed between the at least two extensile protrusions.

14. The method of claim 11, wherein the medical device is disposed proximate to the at least two extensile protrusions.

15. The method of claim 11, wherein the at least two extensile protrusions are positioned proximate to each other to form a first pair of extensile protrusions and extend respectively from opposite walls of the catheter.

16. The method of claim 15, further comprising:

inflating at least another two extensile protrusions extending respectively from opposite walls of the catheter to expand outwardly in opposite directions to be in touch with the walls of the body lumen to provide stability to the catheter inside the body.

17. The method of claim 11, wherein:

at least one of the at least two extensile protrusions includes a conductive top such that, when inflated, the at least one of the at least two extensile protrusions is in touch with the body lumen at the conductive top and forms an electrical path into/from the body.

18. The method of claim 11, wherein inflating the at least two extensile protrusions outwardly comprises expanding a first extensile protrusion of the at least two extensile protrusions at a first length and expanding a second extensile protrusion of the at least two extensile protrusions at a second length different from the first length.

* * * * *